United States Patent [19]

Johnson

[11] 4,067,322
[45] Jan. 10, 1978

[54] DISPOSABLE, PRE-GEL BODY ELECTRODES

[76] Inventor: Joseph H. Johnson, 3611 Terminal Court South, Seattle, Wash. 98144

[21] Appl. No.: 653,227

[22] Filed: Jan. 28, 1976

Related U.S. Application Data

[63] Continuation of Ser. No. 490,082, July 19, 1974, abandoned.

[51] Int. Cl.² .............................................. A61B 5/04
[52] U.S. Cl. .......................... 128/2.06 E; 128/2.1 E; 128/417; 128/DIG. 4
[58] Field of Search .............. 128/2.06 E, 2.1 E, 404, 128/417, 418, DIG. 4

[56] References Cited

U.S. PATENT DOCUMENTS

| | | | |
|---|---|---|---|
| 3,701,346 | 10/1972 | Patrick et al. | 128/2.06 E |
| 3,805,769 | 4/1974 | Sessions | 128/2.06 E |
| 3,828,766 | 8/1974 | Krasnow | 128/2.1 E |
| 3,830,229 | 8/1974 | Johnson | 128/2.06 E |
| 3,834,373 | 9/1974 | Sato | 128/2.06 E |
| 3,848,600 | 11/1974 | Patrick et al. | 128/417 |

*Primary Examiner*—Robert W. Michell
*Assistant Examiner*—Lee S. Cohen
*Attorney, Agent, or Firm*—Seed, Berry, Vernon & Baynham

[57] ABSTRACT

A disposable, pre-gel body electrode for short term use has a self-contained electrolyte gel-impregnated pad therein sealed with a cap which minimizes electrolyte dry-out.

3 Claims, 2 Drawing Figures

DISPOSABLE, PRE-GEL BODY ELECTRODES

This is a continuation of application Ser. No. 490,082, filed July 19, 1974, now abandoned.

BACKGROUND OF THE INVENTION

1. Field of the Invention

This invention relates to a disposable body electrode having a self-contained electrolyte gel therein.

2. Prior Art Relating to the Disclosure

Disposable body electrodes for diagnostic purposes having a self-contained electrolyte gel or paste have been widely used. The problem associated with these electrodes is dry-out or evaporation of the gel prior to use of the electrodes. This is particularly the case when the gel is contained within the body of the electrode by a strippable membrane such as disclosed in U.S. Pat. Nos. 3,515,619; 3,170,459; 3,487,821; 3,590,810; 3,518,984; and 3,602,216. Hermetic sealing of the electrodes in foil packaging, which is illustrated by U.S. Pat. No. 3,692,216, has been used to alleviate this problem. U.S. Pat. Nos. 3,696,807, 3,701,346 and 3,713,435 disclose disposable body electrodes having a self-contained gel and a protective cover over the gel or gel-impregnated pad.

SUMMARY OF THE INVENTION

This invention relates to a disposable body electrode, preferably for short term use, having a self-contained electrolyle gel therein. The electrode includes: (1) a flexible, non-conductive sheet having an adhesive coating on one surface for contact with the skin, the sheet having an aperture formed therein providing a cavity for holding an electrolyte gel-impregnated pad; (2) a stiff but flexible, nonconductive disc secured to the non-conductive sheet material over the aperture; (3) an electrically conductive connector secured to the stiff but flexible disc over the aperture; (4) an electrolyte gel-impregnated pad having a thickness greater than the thickness of the flexible, non-conductive sheet secured to the electrically conductive conector; and (5) a cap over the pad isolating the electrolyte gel from the atmosphere and minimizing dry-out thereof, the top rim of the cap forming an adhesive seal with the adhesive-coated lower surface of the stiff but flexible disc and the sidewalls of the cap forming a frictional seal with the sidewalls of the aperture.

The objects of this invention are to provide a disposable body electrode having a self-contained electrolyte gel wherein the non-conductive sheet and cap form a frictional seal therebetween to minimize dry-out of the gel; to provide a disposable body electrode having a cap over a gel-impregnated pad which does not require a mechanical connection to hold it in place; to provide a disposable body electrode having a gel-impregnated pad over which is disposed a replaceable cap sealing the gel-impregnated pad against contact with the atmosphere; and to provide an economical, disposable, pre-gel electrode suitable for short term use.

DESCRIPTION OF THE PREFERRED EMBODIMENTS

Figure 1:
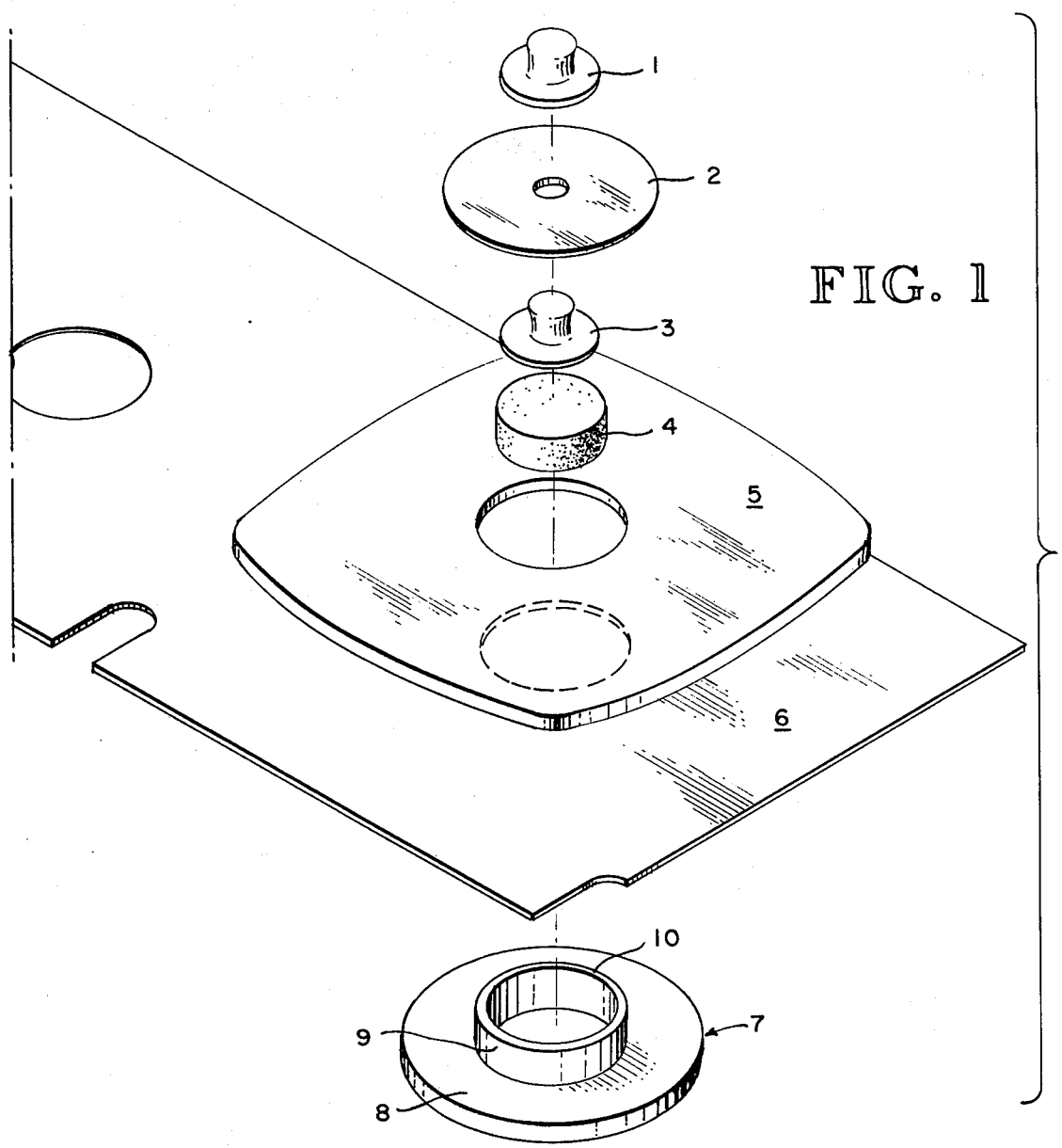
FIG. 1 is an exploded view of the components of the body electrode assembly of this invention.

Referring to FIG. 1 for an exploded view of the components of the electrode assembly, a centrally apertured, flexible, plastic foam sheet 5 or other suitable flexible material having a pressure-sensitive skin adhesive coated on the underside thereof functions to hold the remainder of the electrode assembly against the skin of the patient. The sheet may have a thickness ranging from 1/16 inch to ¼ inch or more so that when the aperture is cut therein, a cavity is formed in the sheet for retention of an electrolyte gel or gel-impregnated pad.

A stiff but flexible disc 2 of smaller size than the sheet 5 is bonded to the surface of sheet 5 opposite the adhesive-coated surface thereof. Preferably, the disc has an adhesive coating on one surface thereof for securing the disc to sheet 5 over the aperture.

An electrical connector, such as a male snap fastener of conventional variety, is secured to that portion of the disc covering the aperture. The snap connector is composed of an inner electrically conductive disc 3 of steel, silver or silver-plated metal which extends through the flexible disc 2. An outer electrically conductive disc 1 receives the portion of the conductive disc 3 projecting through disc 2, forming a mechanical and electrical connection between disc 1 and disc 3. An insulated wire having a female snap connector on one end thereof (not shown) may be used to connect the electrode to the desired diagnostic instrument. Other suitable connectors may also be used.

Figure 2:
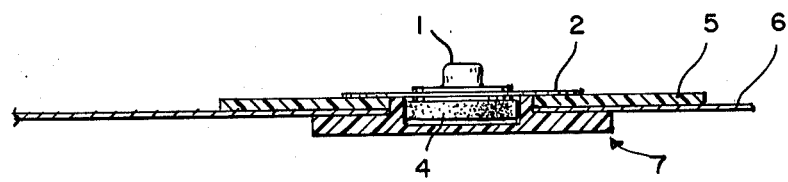
FIG. 2 is a vertial cross-sectional view of the electrode assembly illustrating the integral seal formed between the sealing cap and the non-conductive sheet.

An open-celled, plastic foam pad 4 of polyethylene, or other suitable plastic foam, impregnated with a suitable conductive electrolyte gel is secured to disc 3 as illustrated by FIG. 2. The pad 4 is of a thickness to project slightly beyond the plane formed by the adhesive-coated surface of sheet 5. When the electrode assembly is affixed to the skin of the patient, the pad 4 is slightly compressed against the skin surface, forming an effective and continuous electrical contact therewith.

A peel-off paper 6 having a central aperture of a diameter substantially the same as the diameter of the aperture in sheet 5 is applied to the adhesive coating of the sheet 5 to protect the adhesive until the electrode is ready for use. The paper 6 extends, preferably, beyond the peripheral edges of the sheet 5 so that it can be readily pulled off when the electrode is ready to be used.

A cap 7 is fitted over the pad 4 to prevent exposure of the pad 4 to the atmosphere, thus keeping the gel moist and minimizing dry-out thereof. An adhesive seal is formed between the top rim 10 of the cap 7 and the lower adhesive-coated surface of disc 2. Also, a frictional seal is formed between the sidewall 9 of the cap and the side-walls of the aperture of sheet 5. Referring to FIG. 2, the cap 7 is essentially hat-shaped in cross-section and consists of a circular disc 8 integrally connected with a short, hollow, vertical cylinder centrally disposed on the top surface thereof. The outer diameter of the cylinder is slightly greater than the diameter of the aperture in sheet 5 so that when the cap is pressed in place over the gel-impregnated pad, a frictional seal is formed between the sidewall 9 of the cylinder and the sidewall of the aperture of sheet 5. The height of the cylinder is approximately equal to or greater than the height of the gel-impregated pad 4. Preferably, when the cap 7 is sealed in place, the top surface of the disc 8 does not compress the pad 4 against the disc 3. As mentioned earlier, the pad 4 is secured to the underside of disc 3 by adhesive or mechanical bonding.

The top surface or rim of the cylinder extends into contact with the under surface of disc 2, which is preferably adhesively coated so as to form an adhesive seal between the cap 7 and the disc 2, isolating the gel-impregnated pad from exposure to the surrounding atmosphere.

The disc 8, when the cap is in place over the pad 4, overlaps the peel-off paper 6 so that peeling off the paper 6 pops the cap loose from the disc 2 and sheet 5, allowing immediate service of the electrode. If desired, portions of the disc 8 may be adhesively adhered to the paper 6 so that they can be removed as a unit.

The electrode assembly of this invention is inexpensively and easily manufactured, reliable and provides adequate service for short term use. The electrode is assembled by die cutting a strip of foam sheet plus liner paper with a two-level die, one level of which cuts through the sheet 5 and liner paper 6 to form a central aperture therein, while the second level cuts only through the sheet 5 around the aperture. The disc 2 is then placed over the aperture of the sheet 5, and the disc 2 and sheet 5 adhesively bonded together. The inner and outer portions of the electrical snap connector (3 and 1) are then pressed into place, the gel-impregnated pad is affixed to the underside of disc 3, and the cap 7 is pressed into place.

The embodiments of the invention in which a particular property or privilege is claimed are defined as follows:

1. A disposable, skin-contacting body electrode having a self-contained electrolyte gel therein, comprising:
   a flexible, non-conductive foamed sheet material having a thickness ranging from one-sixteenth to one-fourth inch, an aperture therein with sidewalls the thickness of the foamed sheet material, an adhesive-coated lower surface for contacting the skin surface and a non-adhesive-coated upper surface;
   a semi-rigid disc overlying the aperture and adhesively secured to the portion of the non-adhesive coated upper surface of the foamed sheet material surrounding the aperture to form an open-ended, cup-shaped cavity with the sidewalls of the aperture forming the sidewalls of the cavity and the semi-rigid disc overlying the aperture forming the base of the cavity;
   a pad impregnated with an electrolyte gel inserted within the cavity formed by the non-conductive sheet material and disc, the pad having a thickness greater than the thickness of the non-conductive sheet material so that when the electrode is adhesively secured to the skin the pad is compressed against the surface of the skin;
   an electrical terminal extending through and secured to the disc, making electrical contact with the gel-impregnated pad;
   a strippable sheet completely covering the adhesive-coated surface of the foamed sheet material so as to not expose the adhesive-coated surface of the foamed sheet material until the electrode is ready for application to the skin; and
   a removable cylindrical cap closed at one end and open at the other end, the cap covering the gel-impregnated pad until the electrode is ready for application to the skin and having a sidewall terminating in a rim at the open end, the outer diameter of the sidewall being slightly greater than the diameter of the aperture in the foamed sheet material so as to frictionally engage therewith to isolate the gel-impregnated pad from contact with the atmosphere and thereby minimize loss of moisture from the electrolyte gel, and the height of the sidewall being equal to or greater than the thickness of the gel-impregnated pad so as not to compress the pad when the cap is in place over the pad.

2. The disposable, skin-contacting body electrode as in claim 1 wherein the disc is adhesively coated on the surface secured to the sheet material for adhesively bonding the disc to the upper surface of the foamed sheet material and wherein the rim of the cap contacts the adhesive-coated surface of the disc to further isolate the gel-impregnated pad from contact with the atmosphere.

3. The disposable, skin-contacting body electrode of claim 1 wherein the closed end of the cap includes an integral, transversely extending disc closing the one end of the cap and having a diameter substantially greater than the diameter of the cylindrical cap such that it extends over the strippable sheet so that when the strippable sheet is removed from the adhesive coated surface of the foamed sheet material the cap is also removed.

* * * * *